United States Patent
Claassen et al.

(10) Patent No.: US 9,514,284 B2
(45) Date of Patent: Dec. 6, 2016

(54) GROUP COACHING SYSTEM AND METHOD

(75) Inventors: Arjan Claassen, Eindhoven (NL); Frank Wartena, Eindhoven (NL)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 733 days.

(21) Appl. No.: 12/595,988

(22) PCT Filed: Apr. 17, 2008

(86) PCT No.: PCT/IB2008/051480
§ 371 (c)(1),
(2), (4) Date: Oct. 15, 2009

(87) PCT Pub. No.: WO2008/129479
PCT Pub. Date: Oct. 30, 2008

(65) Prior Publication Data
US 2010/0112536 A1  May 6, 2010

(30) Foreign Application Priority Data
Apr. 20, 2007  (EP) .................................... 07106627

(51) Int. Cl.
| G09B 19/00 | (2006.01) |
| G06F 19/00 | (2011.01) |
| G09B 5/00 | (2006.01) |
| A63B 24/00 | (2006.01) |
| A63B 71/06 | (2006.01) |

(52) U.S. Cl.
CPC ....... *G06F 19/3481* (2013.01); *A63B 24/0075* (2013.01); *G09B 5/00* (2013.01); *A63B 24/0062* (2013.01); *A63B 71/0686* (2013.01); *A63B 2024/0081* (2013.01); *A63B 2225/20* (2013.01)

(58) Field of Classification Search
CPC ............ G09B 19/00; G09B 3/00; A63B 24/00
USPC ........................................................ 434/258
See application file for complete search history.

(56) References Cited

U.S. PATENT DOCUMENTS

| 4,703,445 A | 10/1987 | Dassler |
| 5,137,501 A | 8/1992 | Mertesdorf |
| 6,259,944 B1 | 7/2001 | Margulis |
| 6,458,060 B1 | 10/2002 | Watterson |
| 6,607,493 B2 | 8/2003 | Song |
| 6,644,976 B2 | 11/2003 | Kullok et al. |
| 6,672,991 B2 | 1/2004 | O'Malley |
| 7,063,644 B2 | 6/2006 | Albert et al. |
| 2002/0132215 A1* | 9/2002 | Casey-Cholakis et al. .. 434/350 |
| 2006/0030458 A1 | 2/2006 | Heywood |
| 2006/0058155 A1 | 3/2006 | Kumar |

FOREIGN PATENT DOCUMENTS

| CN | 1263527 C | 7/2006 |
| GB | 2331711 A | 6/1999 |

(Continued)

*Primary Examiner* — Kesha Frisby

(57) ABSTRACT

Group coaching system includes at least a first and a second coaching device, the first device being configured to provide respective first user coaching information to a respective user of the first device, and the second device being configured to provide respective second user coaching information to a respective user of the second device, wherein the system is configured to provide a group coaching of the users of the devices utilizing the respective user coaching information provided by the coaching devices.

18 Claims, 5 Drawing Sheets

(56) References Cited

FOREIGN PATENT DOCUMENTS

| WO | 0029072 A2 | 5/2000 |
|---|---|---|
| WO | 0032088 A1 | 6/2000 |
| WO | 0187426 A2 | 11/2001 |
| WO | 0215985 A1 | 2/2002 |
| WO | 2005032363 A1 | 4/2005 |
| WO | 2005082472 A1 | 9/2005 |
| WO | 2006053349 A1 | 5/2006 |
| WO | 2006094288 A2 | 9/2006 |

* cited by examiner

GROUP COACHING SYSTEM AND METHOD

FIELD OF THE INVENTION

The invention relates to a novel group coaching system, and a method to provide a coaching system.

BACKGROUND OF THE INVENTION

WO2005/082472 discloses an audio pacing device, configured to play an audio signal having a predetermined tempo. During operation, the audio signal can be selected for increasing, decreasing or maintaining a particular user exercise level of intensity. For example, such a device can be used to coach individual exercisers with a personalized training program.

Known personalized training devices as such are very helpful for people during their exercises, however when exercising outdoors, a group of exercisers will probably not be able to stay together if every exerciser follows his/her own personal training program.

SUMMARY OF THE INVENTION

The present invention aims to provide a novel coaching system.

According to an embodiment, there is provided a group coaching system, comprising at least a first and a second coaching device, the first device being configured to provide respective first user coaching information to a respective user of the first device, and the second device being configured to provide respective second user coaching information to a respective user of the second device, wherein the system is configured to provide a group coaching of the users of the devices utilizing the respective user coaching information provided by the coaching devices.

The invention is based on the notion of the above-mentioned problem of known training devices, in that a group of exercisers will not be able to stay together if every exerciser follows his/her own personal training program, using a respective training device. The present invention solves this problem in a simple manner, by providing a group coaching system. For example, the group coaching can involve: association of the users of the devices with respect to each other, to form a group of users, wherein the coaching devices are configured to handle the users as a group. For example, the coaching devices can be configured to provide a virtual higher hierarchy group coaching layer that overlays individual (lower hierarchy) virtual coaching domains relating to the users individually.

According to a preferred embodiment, the coaching devices can be configured to cooperate, to provide a suitable group coaching of the various users of the devices. In particular, the devices can be configured to communicate with each other, preferably during a group coaching process, to transmit group coaching information and/or user performance related information between the devices.

In an embodiment, the system's group coaching can be aimed at or consist of providing the same training program to each of the users of the devices.

Also, in an embodiment, the group coaching, provided by the system, can be aimed at each of the users moving with a certain group speed along the same path.

For example, the group coaching, provided by the system, can involve all users having to move with the same group speed, as a group of users, for example in case the users are physically near one another, particularly in view or in sight of each other, for example moving along the same track or path.

An embodiment of the invention provides a method to provide a coaching system, the method comprising:

providing a plurality of coaching devices, the devices being configured to provide respective coaching information to respective users, wherein the method includes the plurality of coaching devices providing a group coaching of the users. Thus, the users can be coached as a group of users, for example such that the users can exercise together and obtain benefits of being coached by their devices. For example, the method can utilize a group coaching system according to the invention. Also, there can be provided software comprising machine executable code, configured to carry out a method according to the invention when the machine executable code is executed by a machine. In a further embodiment, such software can be embedded in the plurality of coaching devices, the devices being configured to execute the software. Also, for example, the software or machine readable instructions can be loaded into a coaching device to provide a coaching device of a system according to the invention (particularly, to add functionality to the device such that the device can subsequently operate as a coaching device of a system according to the invention). In a further embodiment, such software or machine readable instructions can be provided to a user of the device via a suitable information carrier, for example storage medium, memory means or disk, or be provided in a suitable data format via a communication network, for example a Wide Area Network, for example Internet.

Also, there is provided a coaching device specifically adapted to be a coaching device of a system according to the invention. The coaching device can be provided to (for example delivered or sold to) a respective user, so that the user can subsequently use his device to cooperate with one or more separate devices of other users, to provide a system according to the invention, in case the respective users desire to be coached as a group of users.

Further advantageous embodiments of the invention are described in the dependent claims. These and other aspects of the invention will be apparent from and elucidated with reference to non-limiting embodiments described hereafter, shown in the drawings.

DETAILED DESCRIPTION OF PREFERRED EMBODIMENTS

Similar or corresponding features are denoted by similar or corresponding reference signs in the present patent application.

Figure 1:
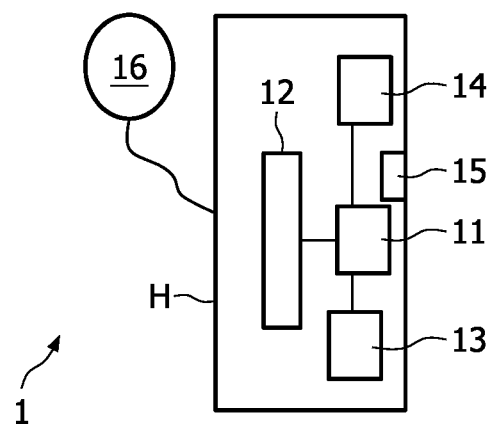
FIG. 1 schematically shows an embodiment of a single coaching device.

FIG. 1 schematically depicts a non-limiting embodiment of a coaching device 1. The device is configured to provide user coaching information to a respective user (not shown) of the device 1. For example, each device 1 can be configured to provide a certain local, virtual coaching domain that is associated to its user, to coach that user. The user can be, for example, an athlete, exerciser, team or group member, and/or a different type of user. The mentioned user coaching information can be specifically associated with a single user, for coaching that user, and can be information that is locally presented to the respective user during operation. In an embodiment, the device 1 is configured such that the respective user coaching information can mainly or only be perceived (and understood) by a user of that device 1, and for example not by bystanders or other individuals.

Each coaching device 1 can be configured in various ways, as will be appreciated by the skilled person. For example, the device 1 can be substantially similar to the device described in WO2005/082472, or be different therefrom. Preferably, the device 1 is portable by a respective user during operation. For example, the coaching device 1 can be adapted to be worn or carried by the user, for example by a neck, arm, wrist or other body part of a user, it can be integrated with clothing worn by the user, and/or can be adapted to be contained in/by clothing or other means that are carried by the user. According to an embodiment, the coaching device 1 can include a dedicated coaching device, being primarily configured to coach the respective user. In another embodiment, the coaching device 1 can have various functions, next to the coaching of the user. The device 1 can be, or be provided by, for example, a PDA (personal digital assistant), cellular phone, watch, position tracking device (for example GPS, i.e. Global Positioning System, device), a user condition monitoring device, and a combination of such and/or other devices.

The present device 1 includes a single housing H having all of the components 11, 12, 13, 14, 15, 16 of the device 1, however, the device 1 can also have an assembly of a number of different/separate housings that include the components.

The device 1 can comprise a controller 11, configured to control operation of the device 1 and for example to carry out device functionality. For example, the controller 11 can be configured to control the providing of coaching information. In an embodiment, the controller 11 can be configured to generate the user coaching information. The device 1 can be provided with a memory 12 to store information, for example coaching information and/or other information. Also, the device 1 can include communication means 14, particularly to communicate with remote communication means (see below). Preferably, the device 1 includes a user interface 15.

Preferably, the device 1 is provided with at least one coaching information provider, to provide respective coaching information to the user of the device 1. In the present embodiment, the coaching information provider can be provided by one or more of the above-mentioned components, particularly by the controller 11: for example, the coaching information provider can be part of the controller 11. The coaching information provider can also be a separate coaching information providing unit that can be controlled by controller 11.

User coaching information can depend on a type of user activity that is to be coached. For example, the user activity can involve a training exercise or sporting activity, for example running, cycling, rowing, et cetera, along a certain path. The device 1 can provide certain individual user coaching information to indicate a desired speed or rhythm to the user, or can be information to encourage the user to speed up, slow down or maintain a present speed. The information provider can be configured to provide the information via audio information, video information, and/or tactile information.

The information provider can include or be connectable to one or more coaching information output units 16, such that the coaching information can be perceived by the user. A coaching information output unit 16 can comprise, for example, speakers, an in-ear or behind-the-ear speaker or headphone, to play audio coaching information to be heard by the user, and/or a display to display video coaching information to the user, and/or a pressure pulse generator to provide tactile coaching information that can be felt by the user.

According to a preferred embodiment, the coaching information is a music rhythm of music that is played by the information provider, for example a beats-per-minute (BPM) signal to indicate a desired user pacing rate or movement rate, for example a user step rate, that is to be followed by the respective user. Also, preferably, the coaching device 1 contains personalized music to be played to provide personal coaching information, for example music signals in one or more suitable format, for example a music compression format, MP3, WAV, AAC, MPEG4, and/or other formats. In a simple embodiment, the individual user coaching information is simply an indication or message to encourage the user to speed up, slow down or maintain a present speed (for example a message like "faster", "slower", "maintain speed").

In an embodiment, the mentioned controller 11 and memory 12 can be separate parts, or be integrated with each other. Also, the communication means 14 of the device 1 can be integrated in the controller 11, or be a separate unit. The controller 11, memory 12 and/or communication means 14 can be provided by suitable hardware, software, microelectronics, and/or other means. The controller 11 can be provided by a suitable processor, computer or computing unit.

The mentioned user interface 15 can include, for example, one or more user operable units, at least one key, switch or knob, a touchpad, touch screen, display, voice operated user interface, keyboard, and/or other user interface. The user interface 15 can be configured to be operated by the user, to enter user commands into the device 1 (for example, to activate the device, change a mode of device operation, and deactivate the device 1). Also, the user interface 15 can be designed to provide information to the user, for example audio and/or visual information. In an embodiment, the user interface 15 can include or be connected to the coaching information output unit 16.

In an embodiment, the communication means 14, or communication unit 14, are configured to provide wireless communication, for example via wireless transmission and/or receiving of signals, radiofrequency signals, optical signals, and/or other signals. The respective communication can include at least one of: Bluetooth™, WIFI (Wireless Fidelity), ZigBee (based on the IEEE 802.15.4 wireless network standard), infrared and/or other communication.

For example, the communication means 14 can be configured to setup a communication network N and/or to communicate via a network N (see FIGS. 2-3), for example a mobile adhoc network, a piconet, WLAN (Wireless Local Area Network), a computer network, telephone network, and/or a different network N.

For example, in the case that each individual coaching device 1 is an assembly of separate parts of units (for example, in the case of a central controller unit 11 being associated with a remote information provider unit and/or remote user interface), the various parts of the device 1 can include suitable respective communication means to communicate with each other.

According to a preferred embodiment, the coaching device 1 can be configured to detect an, particularly instantaneous, training performance of the user of the device. For example, the training performance can include at least one of: a user position, user speed, user speed gradient, user physical state, user posture, user muscle power, and user heart rate.

The coaching device 1 can include a sensor 13 to detect or measure the mentioned training performance. For example, the coaching device 1 can be provided by a user physical state sensor 13, particularly a heart rate sensor 13 or a muscle power sensor. Also, the sensor can include: a user position sensor, user speed sensor, user speed gradient sensor, user posture sensor, or a combination of the mentioned sensors and/or other sensors suitable to detect a certain training performance. For example, the device 1 can include a user position tracker (for example GPS device) that can provide data to be used to determine instantaneous user position, user speed and/or the speed gradient. A user posture sensor can be configured to detect a posture of at least one body part of the user, for example a leg, arm, head, body, and/or to detect a certain variation of that posture.

In a further embodiment, the sensor can be part of the controller 11, or be connected to the controller 11, wherein the controller 11 can be configured to calculate, estimate or determine an instantaneous training performance based on sensor output data. During operation, the sensor 13 can be positioned onto the body of the user (i.e. be in physical contact with the user) to detect the training performance, for example to detect a user heart rate and/or muscle power.

Group Coaching

Preferably (see FIGS. 2, 3, 6), there is provided a system comprising at least two of the coaching devices 1A, 1B, 1C, 1D, 1E, 1F, 1G (at least two separate devices), wherein the devices 1A-1G are configured to cooperate, to provide group coaching to their users. Such cooperation can be achieved in various ways, and particularly makes use of mentioned communication means. For example, the coaching devices 1 can be configured to detect one another's presence via the communications means, and to start their cooperation when they have detected one another's presence. Also, the devices 1 can preferably synchronize with each other during operation to coach a group of users (see below).

According to an example, the coaching devices 1A-1G are configured to provide a virtual high hierarchy group coaching layer that overlays the individual virtual coaching domains relating to the users individually. For example, such virtual high hierarchy group coaching layer can include a virtual group domain that is associated with the users of all of the devices 1A-1G. As an example, a mentioned group coaching layer and each mentioned individual virtual coaching domain can be software implemented, and/or the controllers 11 of the devices 1A-1G can be adapted to provide such virtual layer and domains during operation.

Each of the devices 1A-1G can be configured as has been described above concerning the embodiment of FIG. 1, or can be configured differently.

Also, for example, the various devices 1A-1G of the group of users can have the same configuration, however, this is not essential. For example, the devices 1A-1G can be configured to provide a same type of user coaching information to their users, for example audio information, video information, tactile information. On the other hand, for example, one or more of the devices can play audio signals to coach its/their user(s), and one or more other devices can provide video and/or tactile information to its/their user(s).

For example, at least a first device 1A can be configured to provide respective first user coaching information to a respective user of the first device. For example, according to a non-limiting embodiment, the first user coaching information can be a certain step rate that is to be followed by the first user to maintain a certain speed. The first device 1A is preferably being carried by the first user, in a suitable manner, during operation. A second device 1B can be configured to provide respective second user coaching information to a respective user of the second device. For example, according to a non-limiting embodiment, the second user coaching information can be a certain step rate that is to be followed by the second user to maintain a certain speed. The second device 1B is preferably carried by the second user in a suitable manner, during operation. Similarly, further devices 1C, 1D, 1E, 1F,1G can be configured to provide respective further user coaching information (for example suitable step rates to maintain a certain speed) to a respective users of those further devices.

The system is preferably configured to provide a group coaching of the users of the devices 1A-1G utilizing the respective (individual) user coaching information provided by the coaching devices 1. Preferably, to this aim, the various coaching devices 1A-1G can communicate with each other, to transmit certain group coaching information (particularly information relating to the group as a whole), and/or user performance related information (particularly relating to performance of individual users) between the devices.

For example, in an embodiment, the devices 1A-1G can be configured such that they can operate in a group mode. Besides, for example, at least one of the devices 1A-1G might also be operable in (for example be switched into) a certain non-group coaching mode, to coach its user individually without taking into account group coaching, for example in the case the device is to be used when its user trains alone.

Figure 4:
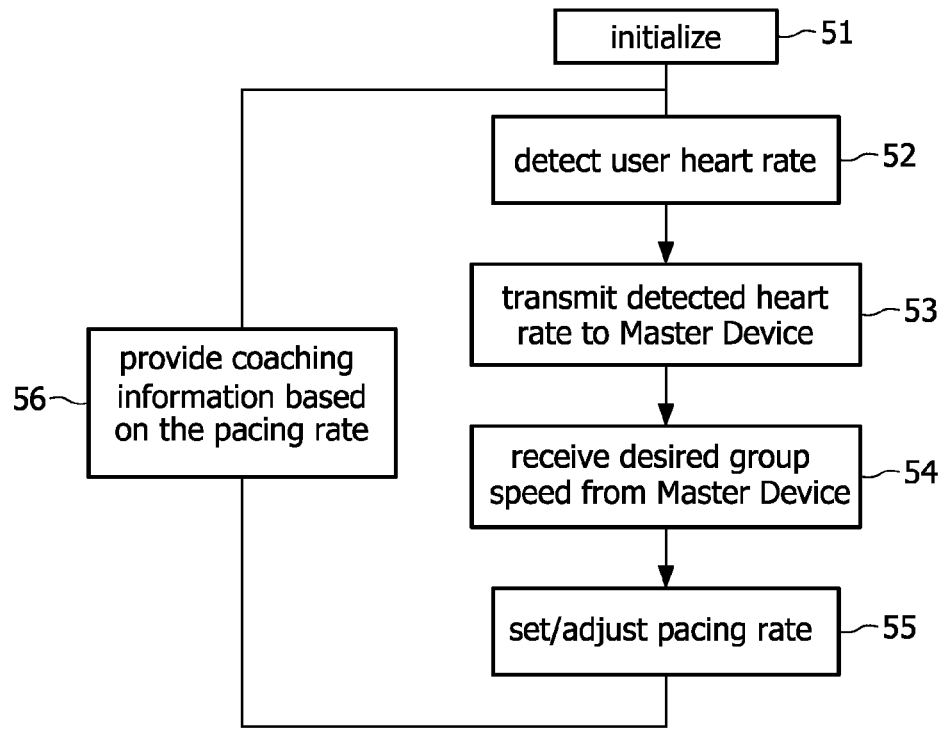
FIG. 4 is a flow chart of an embodiment of operation of a slave coaching device controller, relating to the first embodiment of transmission of information.
Figure 5:
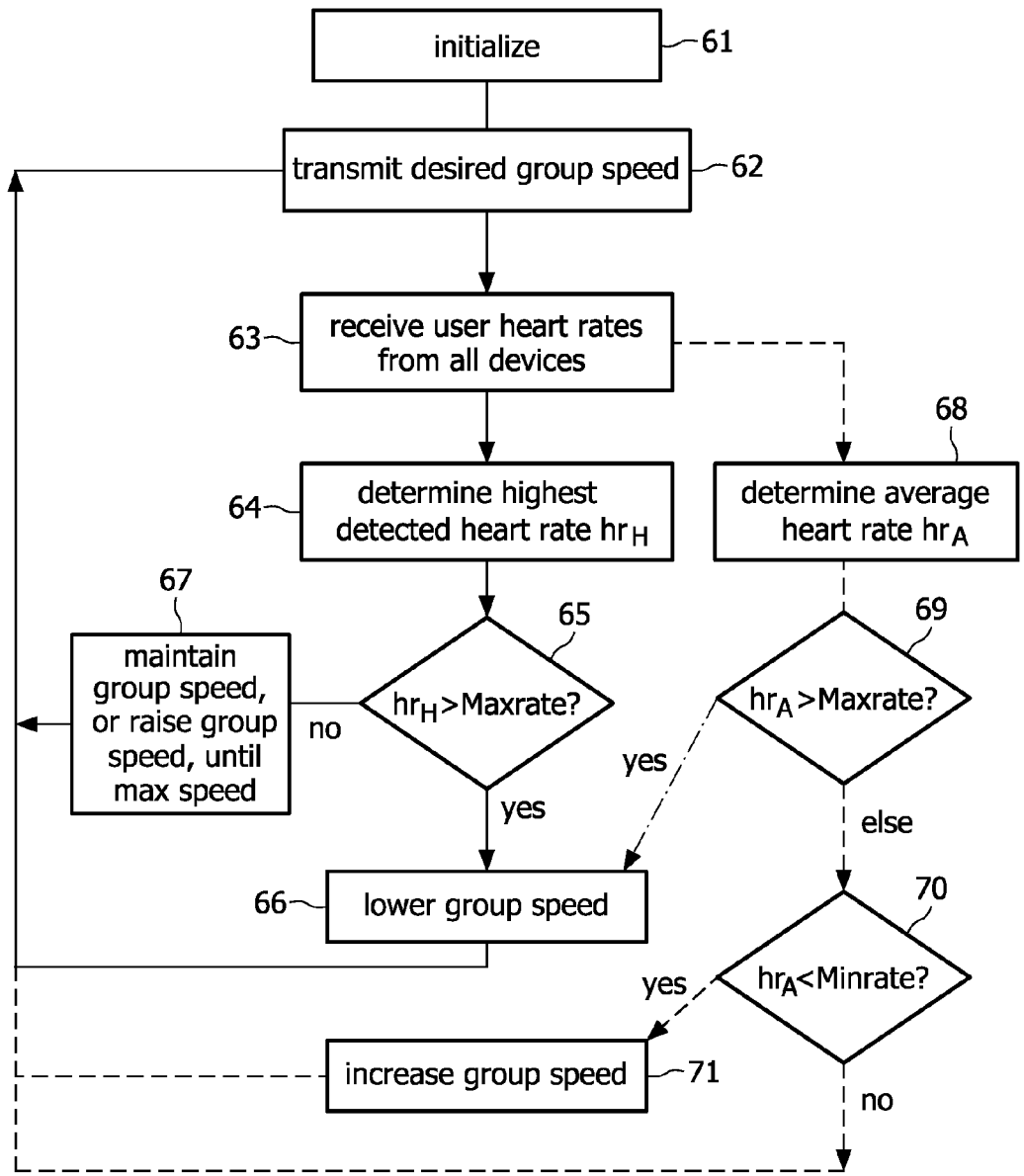
FIG. 5 is a flow chart of an embodiment of operation of a master coaching device controller, relating to the first embodiment of transmission of information.
Figure 7:
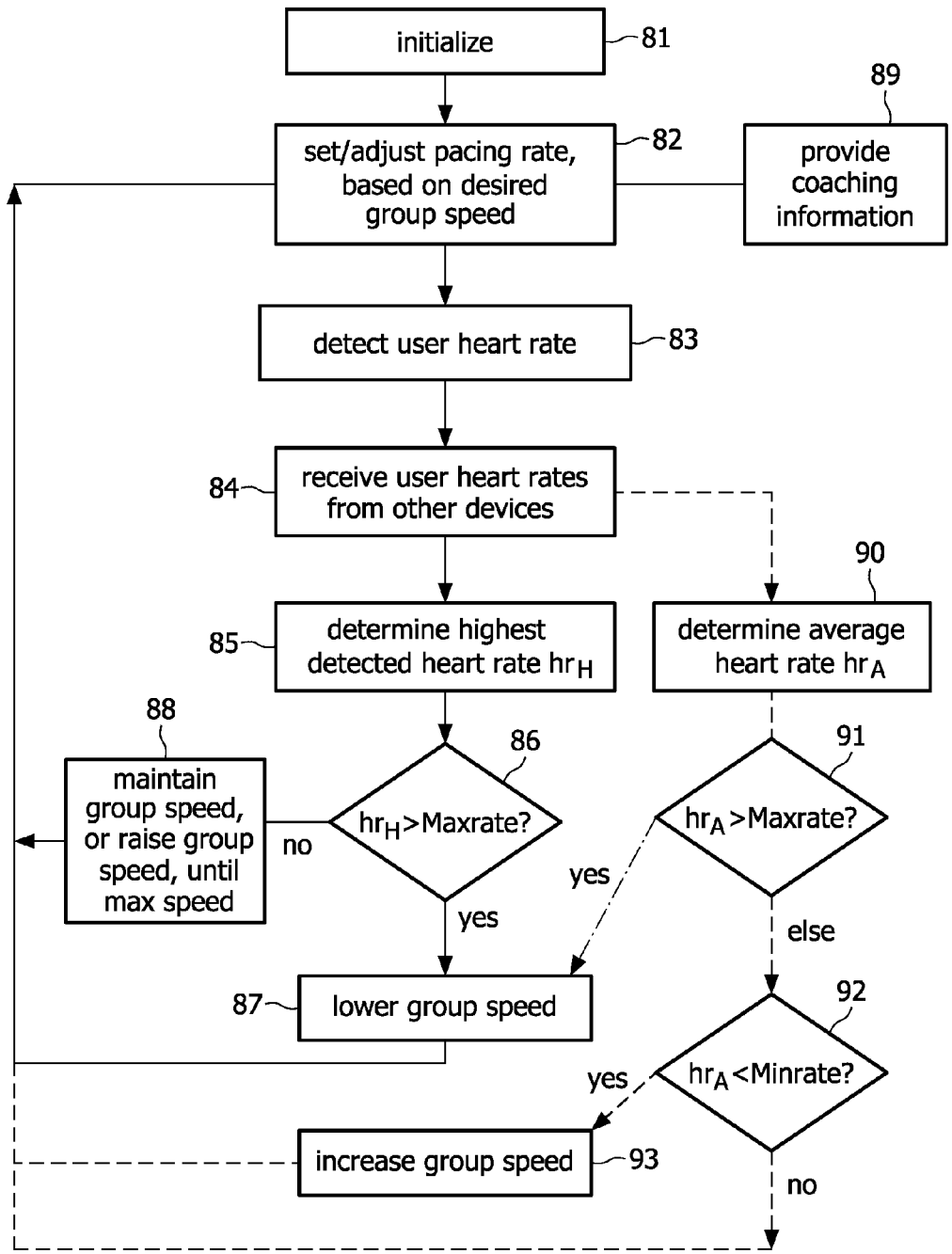
FIG. 7 is a flow chart of operation of a coaching device controller, relating to the second embodiment of transmission of information.

Preferably, the coaching devices that are in their group mode can coach respective users, based on the same group coaching algorithm, particularly such that those users receive the group coaching. For example, the controller 11 of each of the device 1 can hold the same group coaching algorithm; alternatively, the group coaching algorithm can be provided by one of the coaching devices 1, or be distributed or divided in a suitable manner over the coaching devices. Examples of such algorithms are depicted in FIGS. 4, 5, 7. The group coaching algorithm(s) can be configured to determine a group coaching parameter (for example, a group speed, to be achieved by all of the users) based on received user performance related information of the users of the devices 1A-1G.

For example, the group coaching can be aimed at or consist of providing the same training program to each of the users of the devices.

Also, the group coaching can be aimed at each of the users (of the different devices 1A-1G) moving with a certain group speed $v_g$, within a group, along the same path. In an embodiment, the group coaching is aimed at holding the group of users (of the devices 1A-1G) physically together, within a certain area, during operation. For example, the group coaching can involve all users having to move with the same speed $v_g$, in a group (i.e., the users are physically near one another, particularly in view of each other, for example moving in a group or as a team along the same track or path).

Preferably, at least one of the devices 1A-1G can be configured to determine a desired (for example instantaneous) training performance of at least one of the users. Each of the devices 1A-1G can be configured to detect the same type of training performance (for example: heart rate) of a user of the respective device. As follows from the above, a device 1 can be configured to detect/measure the training performance of its own user. Furthermore, a first device 1A can be configured to detect or measure the training performance of the user of an other coaching device 1B, for example in the case that the first device 1A can cooperate or communicate with a suitable training performance sensor that may be provided to detect/measure the training performance of the user of the other coaching device 1B (for example, the latter sensor may be carried by that user).

In an embodiment, the coaching devices 1A-1G can be configured to cooperate to adjust the group coaching, provided to the users of the devices 1A-1G, based on the training performance of the at least one of the users. Also, for example, the coaching devices 1A-1G can be configured to determine a lowest performance from detected training performances of all the users, and to adjust the group coaching based on the lowest performance. Alternatively, for example, the coaching devices 1A-1G can be are configured to determine an average training performance of the detected training performances of all the users, and to adjust the group coaching based on the average performance.

For example, each device 1 can be configured to enter its group mode following a user instruction, for example an instruction "enter group mode" or a similar instruction that has been input by a user via the respective user interface of the device 1. Also, each coaching device 1 can be configured to automatically detect other nearby coaching devices 1, for example via the communication means, wherein the device 1 can enter the group mode automatically if at least one other nearby coaching device 1 has been detected, or—alternatively—ask a respective user (via the user interface) if the device is allowed to enter the group mode if at least one other nearby coaching device 1 has been detected. Also, as an example, each device 1 can include a group mode initialization step when the device 1 enters its group operating mode.

Group Communication

The devices 1A-1G can communicate with each other in different ways, as will be appreciated by the skilled person, for example via a communication network N involving at least one communication link. The mentioned communication link can be provided by above-mentioned communication means 14 of the devices 1A-1G. The communication can be a short range communication, for example having a range having a maximum of about 1 km, particularly a maximum of about 100 m, for example a maximum of about 10 meters, however, this is not essential.

The mentioned communication means 14 of each of the devices 1A-1G can be part of the communication network N, and/or be configured to setup the network N (preferably automatically during a device initialization), and/or be configured to connect to the network N to provide a desired communication over the network N. For example, an appropriate wireless technology that can be used to let the different coaching devices communicate is Bluetooth. It is abundantly available and offers the possibility for 8 devices 1 to communicate (which is already a considerable group of exercisers). In the future, ZigBee could be a viable alternative, which has the added benefit of connecting more devices (up to 65000) and multihop communication (if different coaching devices 1 are not within communication range).

Master-Slave Coaching

Figure 2:
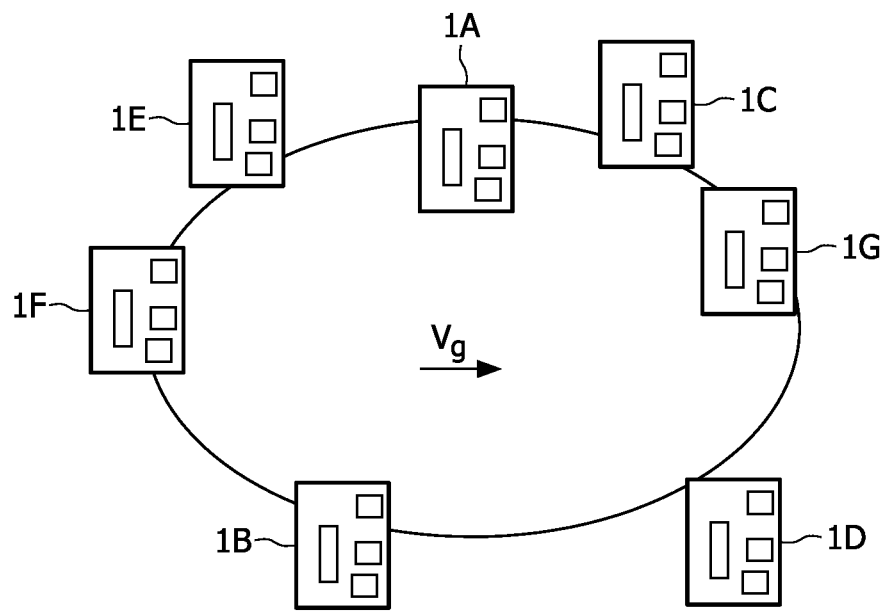
FIG. 2 schematically depicts an embodiment of a group coaching system, during operation.
Figure 3:
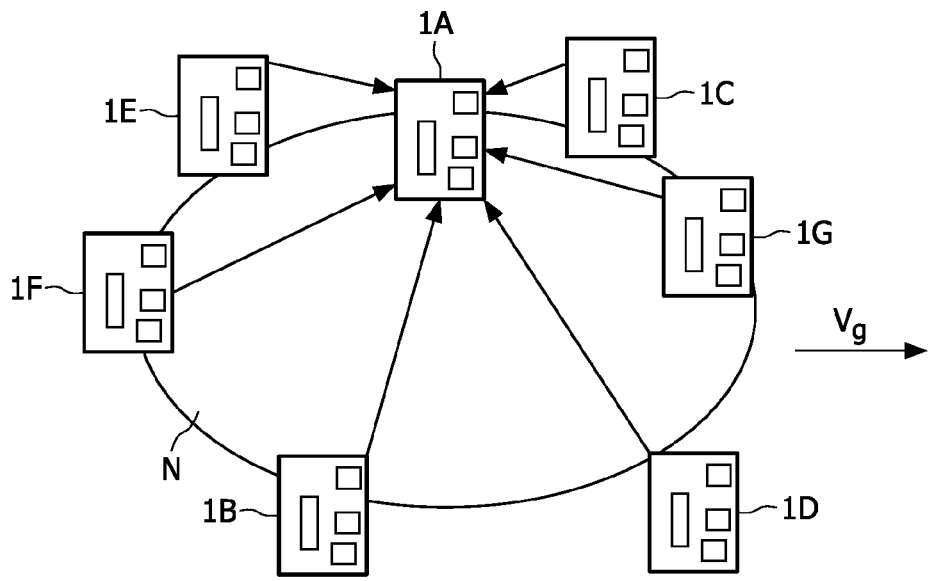
FIG. 3 is similar to FIG. 2 and depicts a first embodiment of transmission of information between the coaching devices.

FIGS. 2-3 depict an embodiment, wherein at least one of the coaching devices 1A (Master device) is configured to determine at least one group coaching parameter, wherein all the devices 1A-1G are configured to cooperate to adjust their respective user coaching information based on the at least one group coaching parameter, to provide the group coaching of the users. For example, a Master device 1A can centrally coordinate the group coaching, and the other devices 1B-1G are Slave devices that can be controlled by the Master device 1A when the devices are in their group modes.

The Master coaching device 1A can be configured to determine the at least one group coaching parameter during operation, and to transmit the at least one parameter to all the other coaching devices (Slaves) 1B-1G, wherein the other devices adjust the respective user coaching information based on the at least one group coaching parameter received from the Master device. Also, each coaching device 1 can transmit a training performance of a respective user to the Master device 1A, wherein the Master device 1A determines the at least one group coaching parameter during operation based on training performances of a plurality of the users, and preferably on all training performances of all of the users. The latter transmission is schematically indicated by arrows in FIG. 3. Herein, the master device 1A can also use a detected training performance of a respective user of the Master device 1A itself, in the case that the Master device 1 detects that performance during operation.

Preferably, a coaching algorithm for the group as a whole can be selected on the Master device 1A. FIG. 4 shows an example of an algorithm that can be carried out by each Slave device during operation. FIG. 5 shows an example of a algorithm that can be carried out by the Master device during operation. I an embodiment, the Master device can be configured to control the Slave devices (for example by transmission of a suitable control message) to select a desired Slave coaching algorithm. For example, each device 1 can contain several coaching algorithms that can be selected to provide a desired coaching, for example a first algorithm relating to coaching based on detected user heart rates, a second algorithm relating to coaching based on detected user speeds, et cetera.

As follows from FIG. 4, in an embodiment, each Slave device can carry out an initialization step 51, for example including an optional self-testing phase, an optional battery check, and preferably including a setting of the operating mode of the device. For example, the initialization step 51 can include setting the device in a Slave group coaching mode and/or a selection of a desired coaching algorithm in the case that more than one algorithm is available.

The Slave device can carry out a step 52 of detecting a user performance, for example a user heart rate (as in the present embodiment). In a transmission step 53, the Slave can transmit the detected user performance (for example heart rate) to the Master device 1A. The Slave device can carry out a step 54 of receiving group coaching information, for example a desired group speed, from the Master device 1A. Depending on the received group coaching information, the Slave device can then set and/or adjust respective individual user coaching information (for example a pacing rate, BPM rate), in step 55, and provide the individual user coaching information (that is based on the received group coaching information) to the respective user, in step 56. These steps 51-56 can be carried out in the order shown in FIG. 4, or in a different order.

For example, in a particular embodiment, a Slave device can increase or decrease a respective pacing rate (or BPM rate) in the case the Slave device determines (in step 55), that a previously set pacing rate (or BPM rate) is too low or too high, respectively, for the user, to achieve the desired group speed. Also, the Slave device can maintain a respective pacing rate (or BPM rate) in the case the Slave device determines (in step 55), that a previously set pacing rate (or BPM rate) is substantially appropriate for the user, to maintain the desired group speed.

FIG. 5 shows a non-limiting example of a Master algorithm that can be executed by the Master device 1A. Therein can also be provided an initialization step 61, for example including bringing the device 1A into a Master group coaching mode. Also, this initialization step 61 can include a selection of a desired coaching algorithm in the case that more than one algorithm is available.

For example, the Master device 1A can transmit group coaching information, for example a desired group speed, to the Slave devices 1B-1G (step 62). Also, the Master device 1A can receive user performances (for example heart rates) that are transmitted by the Slaves (step 63). Based on the received user performances, the Master device can determine to adjust the group coaching information that is to be transmitted.

For example, in an embodiment, there can be a step 64 wherein the Master determines the highest heart rate $hr_H$ of detected heart rates of the users of the group. In case this highest heart rate $hr_H$ is higher than a predetermined maximum allowable heart rate "Maxrate" (step 65), the Master can lower a group coaching parameter, for example desired group speed (step 66), such that training intensity is decreased for all of the users.

In an embodiment, the Master can determine that the highest heart rate $hr_H$ is not higher than the predetermined maximum allowable heart rate "Maxrate" (step 65). In that case, the Master can maintain or increase the group coaching parameter, for example desired group speed (step 66), such that training intensity is maintained or increased, respectively, for all of the users.

Dashed lines in the FIG. 5 flow chart show another example of Master device operation. There can be a step 68 wherein the Master determines an average heart rate $hr_A$ from all detected heart rates of all of the users. In case the average heart rate $hr_A$ is higher than a predetermined maximum allowable heart rate "Maxrate" (step 69), the Master can lower a group coaching parameter, for example desired group speed (step 66), such that training intensity is decreased for all of the users. In case the average heart rate $hr_A$ is lower than a predetermined minimum allowable heart rate "Minrate" (step 70), the Master can increase a group coaching parameter, for example desired group speed (step 71), such that training intensity is increased for all of the users. Else, in case the average heart rate $hr_A$ is within a desired range (between Maxrate and Minrate), the Master device can maintain the set group coaching parameter, for example the desired group speed.

Besides, in an embodiment, the Master device 1A as such can also carry out at least part of a Slave algorithm (see FIG. 4) to coach a user of the Master device, as will be appreciated by the skilled person (in that case, for example, the slave algorithm of the device 1A can communicate with the master algorithm internally in the device 1A). Thus, the Master device 1A can also have Slave functionality by itself, the slave functionality being controlled by the Master algorithm of the Master device.

For example, in an embodiment, the devices 1A-1G of the group can be configured such that when they are switched on, they can be put in "group" mode, wherein one device is being selected as Master or supervisor device 1A (in case of the fixed supervisor setup). Preferably, all other devices 1B-1G connect to Master device 1A.

For example, when a respective group of users starts exercising, the different devices 1A-1F can send their local use performance measurements to the Master device 1A, wherein this Master device 1A determines or calculates a group training intensity (e.g. average group speed $v_g$) for the group as a whole based on the selected coaching algorithm. This group training intensity can subsequently be sent to the different coaching devices 1A-1G, which adjust their coaching information output in order to keep the users at the required intensity. This process can run real-time and the group training intensity (for example group speed) of the group can be continuously adjusted.

Thus, there can be provided the possibility of different coaching devices 1 communicating with one another, and being configured to make decisions on a coaching algorithm for the group as a whole. There can be provided one supervisor device 1A that decides on the coaching algorithm, as an example, can calculate a required speed for the group of users as a whole based on the measurements of all coaching devices 1. An alternative solution can have a dynamic supervisor, where different devices 1 can assume the role of supervisor during an exercise (e.g. a device of the worst exerciser, for example having a highest heart rate, is selected as supervisor, where the worst exerciser is dynamically determined by the network).

Also, in an embodiment, in the case that a previously selected Master device 1A becomes unavailable during a group coaching process, for example in the case that device 1A is switched off or becomes out of range with respect to the other devices, preferably, a new master device is automatically selected by the remaining coaching devices 1B-1G, from the remaining devices.

Semi-Autonomous Coaching

Figure 6:
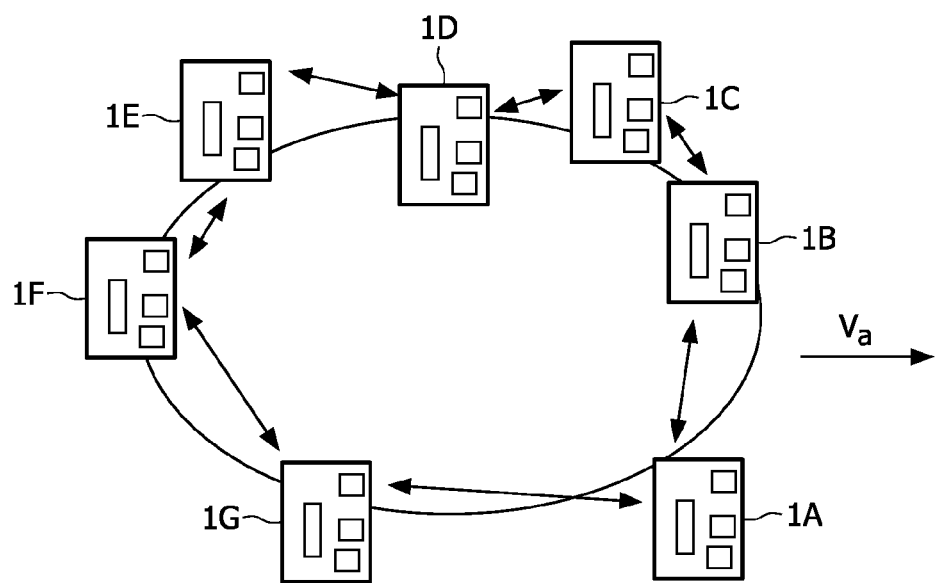
FIG. 6 is similar to FIG. 3 and depicts a second embodiment of transmission of information between the coaching devices.

FIG. 6 depicts an alternative embodiment, wherein the various coaching devices 1A-1G can interact to interchange user performance related information of all users of all devices, but can operate substantially autonomously to coach each respective user based on received coaching information, for example to set and/or adjust group coaching information stored in the respective device 1. In this case, each of the devices 1 can transmit respective user performance information (of the user of that device 1) to all other coaching devices via the network N.

FIG. 6 shows a respective semi-autonomous group coaching algorithm that can be carried out by each coaching device 1A-1G. For example, each controller 11 of each device 1 can execute the same semi-autonomous group coaching algorithm during operation.

There can be provided an initialization step 81, for example including bringing the device 1 into a semi-autonomous group coaching mode. The coaching device 1 can carry out a step 82 to set/adjust individual coaching information (for example a pacing rate) based on a desired group coaching (for example group speed). In this case, for example, each coaching device 1 can determine or calculate the desired group coaching (group speed) by itself. Also, there is provided a step 89 of providing the coaching information (for example individual pacing rate) to the user of the device 1.

In this embodiment, each device 1 carries out a step 83 of detecting a user performance, for example a user heart rate, and of transmission of the detected user performance to all other devices 1. Each device 1 can also carry out a step 84 of receiving user performance information from each of the other devices 1.

For example, according to an embodiment, each device 1 can determine to adjust the group coaching information, for example being stored in that device 1. For example, in an embodiment, there can be a step 85 wherein each coaching device 1 autonomously determines the highest heart rate $hr_H$ of detected heart rates of the users of the group. In case this highest heart rate $hr_H$ is higher than a predetermined maximum allowable heart rate "Maxrate" (step 86), the coaching device 1 can lower a group coaching parameter, for example desired group speed (step 87), such that training intensity is decreased for all of the users. In an embodiment, each device 1 can autonomously determine that the highest heart rate $hr_H$ is not higher than the predetermined maximum allowable heart rate "Maxrate" (step 88). In that case, the coaching device 1 can maintain or increase the group coaching parameter, for example desired group speed (step 88), such that training intensity is maintained or increased, respectively, for the user of the device. Preferably, all coaching devices 1 are configured to modify locally stored group coaching parameters by the same amounts, based on the user performance information of all of the users, by being provided with the same semi-autonomous coaching algorithm.

Dashed lines in FIG. 7 show another example of semi-autonomous coaching device operation. There can be a step 90 wherein each device 1 determines an average heart rate $hr_A$ from all detected heart rates of all of the users. In case the average heart rate $hr_A$ is higher than a predetermined maximum allowable heart rate "Maxrate" (step 91), each device 1 can autonomously lower a locally stored group coaching parameter, for example desired group speed (step 87), such that training intensity is decreased for the respective user. In case the average heart rate $hr_A$ is lower than a predetermined minimum allowable heart rate "Minrate" (step 92), the coaching device 1 can increase the locally stored group coaching parameter, for example desired group speed (step 93), such that training intensity is decreased for the respective user. Else, in case the average heart rate $hr_A$ is within a desired range (between Maxrate and Minrate), the coaching device 1 can maintain the locally set group coaching parameter, for example the desired group speed.

Thus, according to an embodiment, performance measurements relating to all exercisers can be transmitted to all coaching devices 1. Each device 1 can then use the same coaching algorithm, using the same input data (i.e. performance measurements of all users) to coach the individual user of the group.

In above examples, group coaching has been based on detecting and evaluating user heart rates. According to another embodiment, a coaching algorithm can be configured to calculate a group performance, for example the average speed of the group. This determined average speed (i.e. group speed) can then be directly used to coach the individual exercisers. For example, according to a particular embodiment, multiple coaching devices 1 can form a network (preferably wireless) to exchange various parameters, such as heart rate and/or speed of the different exercisers. Based on a selected coaching mode (for example Master-Slave, or Semi-autonomous) the speed for the group as a whole can be calculated (for example centrally by the Master, of locally by each Semi-autonomously operating device). In case of a Master-Slave mode, the centrally determined speed can be subsequently transmitted to all coaching devices 1, which will adjust their local coaching output (e.g. music tempo) to maintain the selected speed of every exerciser individually.

Also, the group coaching that is provided by the system of coaching devices 1 can be modified in other ways, if desired.

The present invention can provide for a group of exercisers to stay together while keeping the benefit of coaching. For example, a single coaching mode can to be selected for the group as a whole. The group coaching can be aimed at: keeping the heart rate of the worst exerciser within the preferred range (all other exercisers will probably have a too low heart rate); keeping the average heart rate of the group within the preferred range (the worst exercisers will probably have a too high heart rate), et cetera.

According to an embodiment, different exercisers might run at different tempos for one single speed (based for example on the size of their steps). Also, different exercisers can have personalized music collections, stored in their individual coaching devices 1. The present invention can combine the exercising in a group (e.g. run at the same speed with a group) with individual coaching (e.g. by adjusting the tempo of personalized music) based on a certain coaching algorithm for the group as a whole.

In an embodiment, prior to the coaching, exercisers can form several sub-groups based on performance, in which case differences within a sub-group will not be very large. This means that every exerciser will get a reasonably optimized exercise while maintaining the added stimulation of exercising together.

The invention can be applied to use individual coaching devices 1 in a group setting, for instance to allow a group of runners to stay together while maintaining coaching behavior and personalized output (e.g. music).

A basic idea behind the invention is to provide at least an algorithm to coach a group of runners at the same time. For example, a group of runners wants to run together. This can mean that they will all have to run at the speed, wherein the heart rate of the slowest (or worst) runner is at a maximally allowed level (i.e. Maxrate). To solve this problem, different devices 1 can form a network and—for example—exchange a speed that can be achieved, or exchange other information (for example heart rates) that can be used to provide the group coaching. In each device 1, this speed can be used as main input of the coaching algorithm. Also, the algorithm can check if the heart rate is not too high (if so exchange a lower speed on the network) and based on that adjust the pace of the music. Also, according to an embodiment, the complete group can run at the same speed, however, not necessarily with all users having the same pace (since the individual pace depends on user proportions/dimensions as will be appreciated by the skilled person).

Besides, for example, in above embodiments it is assumed that each coaching device 1 is associated with a single user, for example in the case of a single athlete carrying the device during training. However, this is not essential, since according to a further embodiment, in a system there can be provided at least two coaching devices 1, the first device being configured to provide respective first user coaching information to at least one respective user of the first device, and the second device being configured to provide respective second user coaching to at least two respective users of the first device. For example, each coaching device 1 can be associated with a respective rowing boat, wherein at least one of the boats has at least one rower and the other boat has at least two rowers, the coaching devices 1 being configured to coach the rowers of all the boats as a group (for example such, that the boats remain near one another during a training exercise, and for example depending on one or more parameters, for example a monitored physical condition of all of the rowers during the exercise).

Although the illustrative embodiments of the present invention have been described in greater detail with reference to the accompanying drawings, it will be understood that the invention is not limited to those embodiments. Various changes or modifications may be effected by one skilled in the art without departing from the scope or the spirit of the invention as defined in the claims.

It is to be understood that in the present application, the term "comprising" does not exclude other elements or steps. Also, each of the terms "a" and "an" does not exclude a plurality. Also, a single processor, controller or other unit may fulfill functions of several means recited in the claims. Besides, a plurality of processors, controllers or other units may fulfill functions of several means recited in the claims. Any reference sign(s) in the claims shall not be construed as limiting the scope of the claims.

The invention claimed is:

1. A system for group coaching a plurality of users, the system comprising:
   a plurality of devices, each of the plurality of users having at least one of the plurality of devices including a same training program, each device comprising:
   a communication link configured to communicate with other devices of the plurality of devices including receiving the same training program for each of the respective users and communicating the detected training performance to the plurality of devices;
   a processor configured to
   detect a training performance of the device's respective user responsive to the training program, and
   adjust the training program for one or more respective users of the plurality of users based on the detected training performance of all of the plurality of users, such that all of the plurality of users are instructed to move with a group speed along a first path so that the plurality of users are physically held together during the group coaching; and
   a user interface configured to provide the instructions to the device's respective user concerning the adjustment of the training program for the device's respective user.

2. The system according to claim 1, wherein the devices cooperate and communicate with each other to transmit the training program and/or the detected training performance related information between the devices.

3. The system according to claim 1, wherein the plurality of devices includes a first master device and the same training program is provided to each of the plurality of users by the master device, and the plurality of devices are configured to autonomously select a second master device when the first master device becomes unavailable.

4. The system according to claim 3, wherein at least one of the plurality of devices is configured to detect the training performance of at least one of the plurality of users and transfer the detect training performance to the master device.

5. The system according to claim 1, wherein the adjusting is based on the detected training performances of a plurality of the users.

6. The system according to claim 1, wherein the processor autonomously adjusts the training program and the adjusting is based on a lowest training performance determined from the detected training performances of the plurality of users.

7. The system according to claim 1, wherein the adjusting is based on an average training performance determined by an average performance of the detected training performances of the plurality of users, and the adjusting of the program includes communicating instructions to the users via the user interface of each user's respective device in the form of one or more of a visual message, an audio message, a tactile message, and a musical message.

8. The system according to claim 1, wherein the training performance includes at least one of: a user position, user speed, user speed gradient, user physical state, user posture, user muscle power, and user hear rate.

9. The system according to claim 1, wherein adjusting of the training performance is directed to keeping the users physically together within a predetermined area, including in view of each other.

10. The system according to claim 1, wherein the adjusting is based on at least one group coaching parameter including an average group speed of the group of users.

11. The system according to claim 10, wherein the at least one group coaching parameter is determined when
   a first of the plurality of devices transmits the at least one group coaching parameter to each of the plurality of devices, and
   at least a second of the plurality of devices adjusts its training program based on the at least one group coaching parameter received from the first device.

12. The system according to claim 10, wherein each of the plurality of devices transmits the training performance of its user to a master device, which determines the at least one group coaching parameter based on the detected training performances of all the users.

13. The system according to claim 10, wherein each of the plurality of devices autonomously determines the at least one group coaching parameter.

14. The system according to claim 10, wherein each device comprises a computer readable storage medium comprising machine executable code, which when executed configures the device to
   communicate with other devices,
   receive the training program for its respective user,
   detect the training performance of at least one of the users,
   adjust the training program based on the detected training performance, and
   communicate instructions to the device's respective user concerning the adjustment of the training program.

15. The system according to claim 1, wherein one of the plurality of devices is selected to be a coaching device.

16. The system according to claim 1, wherein at least one of the plurality of devices is configured to detect at least one other device's presence via the communication link and is further configured to start communicating with at least one other device once they detect the at least one other device's presence.

17. A training device for group coaching a plurality of users each having a respective training device, the training device comprising:

a communication link configured to inter-communicate with each of the plurality of devices including receiving a same training program for each of the respective users;

a processor configured to
- detect a training performance of the device's respective user responsive to at training program, and
- adjust the training program for one or more respective users of the plurality of users based on the detected training performance of all of the plurality of users, such that all of the plurality of users are instructed to move with a group speed along a first path so that the plurality of users are physically held together during the group coaching; and a user interface configured to provide the instructions to the device's respective user concerning the adjustment of the training program for the device's respective user.

18. A computer readable non-transitory storage medium comprising machine executable code, which when executed by a computer configures a system for group coaching a plurality of users each having a respective training device, the training device comprising:

a communication link configured to communicate with each of the plurality of devices in possession of the plurality of users, a processor configured to
- receive the training program for its respective user,
- detect the training performance of at least one of the users, and
- adjust the training program based on the detected training performance of all of the plurality of users, such that all of the plurality of users are instructed to move with a group speed along a first path so that the plurality of users are physically held together during the group coaching; and a user interface configured to provide the instructions to the device's respective user concerning the adjustment of the training program for the device's respective user.

* * * * *